United States Patent [19]
Lui et al.

[11] Patent Number: 5,739,380
[45] Date of Patent: Apr. 14, 1998

[54] (METH)ACRYLATES CONTAINING FLUOROALKENYL GROUPS, THEIR PREPARATION AND USE

[75] Inventors: Norbert Lui; Wolfgang Podszun, both of Köln, Germany

[73] Assignee: Bayer Aktiengesellschaft, Leverkusen, Germany

[21] Appl. No.: 649,043

[22] Filed: May 16, 1996

[30] Foreign Application Priority Data

May 23, 1995 [DE] Germany .................. 195 18 865.9

[51] Int. Cl.⁶ .................................................. C07C 69/52
[52] U.S. Cl. ................................... 560/220; 560/225
[58] Field of Search ................................... 560/220, 225

[56] References Cited

U.S. PATENT DOCUMENTS

| | | | |
|---|---|---|---|
| 3,520,863 | 7/1970 | Annello et al. | 560/220 |
| 3,547,861 | 12/1970 | Annello et al. | 560/220 |
| 3,716,577 | 2/1973 | Pittman et al. | 560/220 |
| 3,723,507 | 3/1973 | Annello et al. | 560/220 |
| 4,267,360 | 5/1981 | Ozawa et al. | |
| 5,085,975 | 2/1992 | Mueller . | |

FOREIGN PATENT DOCUMENTS

| | | |
|---|---|---|
| 0 234 724 | 9/1987 | European Pat. Off. . |
| 34 21 511 A1 | 12/1985 | Germany . |

OTHER PUBLICATIONS

Document No. 92:224259 Yoneyama et al. Brit. U.K. Pat. GB2024440 80/01/09–In–house Computer abstract pp. 9–11.

*Primary Examiner*—Joseph L. Schofer
*Assistant Examiner*—N. Sarofim
*Attorney, Agent, or Firm*—Sprung Kramer Schaefer & Briscoe

[57] ABSTRACT

Novel (meth)acrylates containing fluoroalkenyl groups, of the formula (I)

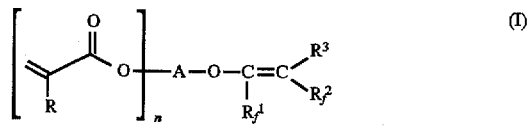

in which

R represents hydrogen or methyl, n represents an integer from 2 to 6,

A represents a (n+1)-valent hydrocarbon radical having 3 to 30 carbon atoms which optionally contains up to 10 oxygen atoms, and $R^1_f$ and $R^2_f$ independently of one another each represent a perfluoroalkyl radical having 1 to 20 carbon atoms, or $R^1_f$ and $R^2_f$ together form a

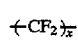

bridge, in which
x represents an integer from 1 to 8, and $R^3$ represents hydrogen, fluorine, chlorine or a perfluoroalkyl radical having 1 to 20 carbon atoms, a process for their preparation, and their use for the preparation of coatings.

3 Claims, No Drawings

(METH)ACRYLATES CONTAINING FLUOROALKENYL GROUPS, THEIR PREPARATION AND USE

The present invention relates to novel (meth)acrylates containing fluoroalkenyl groups, to a process for their preparation from an alcohol containing (meth)acrylate groups and from an olefin containing fluoroalkyl groups, and to their use for the preparation of coatings having hydrophobic and dirt-repellent properties.

Polymerizable compounds containing perfluoroalkyl groups are known (see for example DE-A 3 421 511). Their preparation involves reacting perfluorooctane carbonyl chloride with pentaerythritol triacrylate. A disadvantage is the low stability of the ester bond to hydrolysis.

(Meth)acrylates have now been found which contain fluoroalkenyl groups and are of the formula (I)

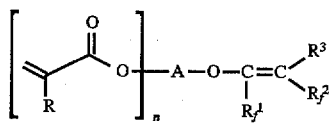

in which

R represents hydrogen or methyl, n represents an integer from 2 to 6,

A represents a (n+1)-valent hydrocarbon radical having 3 to 30 carbon atoms which optionally contains up to 10 oxygen atoms, and $R^1_f$ and $R^2_f$ independently of one another each represent a perfluoroalkyl radical having 1 to 20 carbon atoms, or $R^1_f$ and $R^2_f$ together form a

bridge, in which x represents an integer from 1 to 8, and $R^3$ represents hydrogen, fluorine, chlorine or a perfluoroalkyl radical having 1 to 20 carbon atoms.

In formula (I), n preferably represents an integer from 2 to 5.

Preferred radicals A contain 3 to 12 carbon atoms and optionally up to 6 OH groups and/or optionally up to 8 ether bridges. Particularly preferred radicals A are:

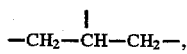

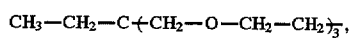

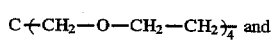 and

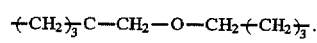.

Preferably, $R^1_f$ and $R^2_f$ independently of one another each represent a perfluoroalkyl radical having 1 to 6 carbon atoms, or together form a

bridge in which x represents an integer from 1 to 5.

$R^3$ preferably represents hydrogen, fluorine, chlorine or a perfluoroalkyl radical having 1 to 6 carbon atoms.

Particularly preferably, $R^1_f$ and $R^2_f$ independently of one another each represent trifluoromethyl or pentafluoroethyl, or together form a

bridge in which x represents an integer from 2 to 4.

$R^3$ particularly preferably represents fluorine, chlorine, trifluoromethyl or pentafluoroethyl.

The present invention also relates to a process for the preparation of (meth)acrylates containing fluoroalkenyl groups, of the formula (I), which is characterized in that an alcohol of the formula (II)

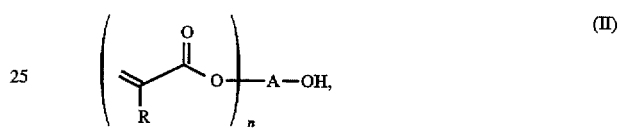

in which

R, n and A have the meaning given for formula (I), is reacted in the presence of a base with an olefin of the formula (III)

in which $R^1_f$, $R^2_f$ and $R^3$ have the meaning given for formula (I) and

X represents fluorine or chlorine.

In the formulae (II) and (III), the preferred and particularly preferred meanings of n, A, $R^1_f$, $R^2_f$ and $R^3$ are the same as those indicated for formula (I).

Alcohols of the formula (II) are in most cases known commercial products or can be prepared in analogy to known compounds. Very particularly preferred alcohols of the formula (II) are glycerol dimethacrylate, glycerol methacrylate acrylate, glycerol diacrylate, pentaerythritol triacrylate and dipentaerythritol pentaacrylate.

Olefins of the formula (III) are likewise in most cases known commercial products or can be prepared in analogy to known compounds.

Very particularly preferred olefins of the formula (III) are perfluoro-(2-methyl-pent-2-ene), hexafluoropropene trimer, 1,1,1,4,4,4-hexafluoro-2,3-dichloro-but-2-ene, perfluorocyclobutene, perfluorocyclopentene, perfluorocyclohexene, perfluorocyclopropene, 1,2-dichloro-tetrafluorocyclobutene, 1,2-dichloro-hexafluorocyclopentene and 1,2-dichloro-octafluorocyclohexene.

Based on 1 mol of alcohol of the formula (II) it is possible, for example, to employ from 1 to 20 mol of an olefin of the formula (III). This quantity is preferably from 1 to 3 mol.

Suitable bases are inorganic and organic bases, for example ammonia, primary, secondary and tertiary amines, pyridines, alkali metal and alkaline earth metal hydroxides and alkali metal and alkaline earth metal carbonates. Organic amines can contain, for example, alkyl groups having 1 to 10 carbon atoms and/or aryl groups having 6 to 10 carbon atoms. Preference is given to triethylamine, dimethylaniline, pyridine, potassium hydroxide, sodium hydroxide, potassium carbonate and sodium carbonate.

The quantity of base is chosen to be at least sufficient to provide for just complete binding of the hydrogen fluoride or chloride which is formed in the course of the reaction. Excesses of base, for example up to 5 equivalents, do not in general cause any problems.

It is advantageous to carry out the process according to the invention in the presence of a solvent. Suitable solvents are aprotic solvents such as methylene chloride, chloroform, carbon tetrachloride, dichloroethane, trichloroethane, tetrachloroethane, benzene, toluene, chlorobenzene, dimethylformamide, tetramethylene sulphone, dimethyl sulphoxide, acetonitrile, glyme, diglyme and tetrahydrofuran. Based on 100 g of alcohol of the formula (II) plus olefin of the formula (III) it is possible, for example, to employ from 40 to 500 ml of an aprotic solvent.

The reaction according to the invention can be carried out, for example, at temperatures in the range from 0° to 80° C., preferably from 10° to 40° C. The pressure is in general not critical. It is possible to operate at atmospheric pressure, subatmospheric pressure and superatmospheric pressure, for example at from 0.1 to 5 bar. It is preferred to operate at atmospheric pressure.

The reaction time can, for example, be between 0.5 and 15 hours.

The process according to the invention can be carried out, for example, by taking the alcohol of the formula (II), the olefin of the formula (III) and the solvent as initial charge and adding the base in portions. The combination of the reactants, the base and, optionally, the solvent can also be carried out by another method.

The mixture present after the reaction can be worked up, for example, by first adding water, separating off the organic phase and removing from this phase any solvent present. It is advantageous to subject the aqueous phase which remains after phase separation to extraction with a water-immiscible solvent and to work up the extract further together with the organic phase. It is also advantageous to dry the organic phase, together if appropriate with the extract from the aqueous phase, prior to removal of solvents, this drying being carried out, for example, with sodium sulphate.

In the case of certain solvents, phase separation may not be achievable by addition of water. In such cases it is advantageous to subject the reaction mixture, to which water has been added, to extraction with a water-immiscible solvent and to work up the extract as indicated above for the organic phase.

In accordance with the process according to the invention, (meth)acrylates of the formula (I) are obtained in high yields of in general more than 80, and frequently more than 90, % of theory.

The (meth)acrylates containing fluoroalkenyl groups, of the formula (I), can be used in order to prepare coatings therefrom.

For this purpose it is possible, for example, to apply the (meth)acrylates of the formula (I), optionally in a mixture with other monomers and/or polymers, dissolved together with a photoinitiator in an inert solvent, to the substrate to be coated, using a knife, and to cure the applied coating with UV light. Examples of suitable photoinitiators are benzoin derivatives, while examples of inert solvents are ketones such as butanone, and esters. When mixtures of (meth) acrylates of the formula (I) with other monomers and/or polymers are employed to prepare the coatings, the content of (meth)acrylates of the formula (I) in these mixtures can for example be from 2.5 to 80% by weight. This quantity is preferably from 5 to 60% by weight.

The coatings prepared in this way are distinguished by great weathering stability, great resistance to hydrolysis and pronounced antiadhesive properties.

EXAMPLES

Example 1

100 g of triethylamine were added dropwise at room temperature to 150 g of glycerol dimethacrylate and 200 g of perfluoro-(2-methyl-pent-2-ene) in 500 ml of acetonitrile. The mixture was stirred at room temperature for 10 hours, and then 500 ml of water were added and the organic phase was separated off. The aqueous phase was subjected twice to extraction with 200 ml of methylene chloride. The combined organic phases were subjected to extraction in succession with 100 ml of water, 100 ml of 1N aqueous hydrochloric acid and 100 ml of water. The organic phase was subsequently dried over sodium sulphate. Removal of the solvent in vacuo gave 270 g of [3-(2-methyl-acryloyloxy)-2-(3,3,3-trifluoro-1-(1,1,2,2,2-pentafluoroethyl)-2-trifluoromethyl-propenyloxy)]-propyl 2-methylacrylate.

Yield: 82% of theory $^{19}$F-NMR data: δ (CDCl$_3$) −56.2, −59.6, −80.6, −113.4 ppm $^1$H-NMR, data: δ (CDCl$_3$) 1.95, (s, 6H), 4.4 (m, 4H), 5.0 (m, 1H), 5.65 (m, 2H), 6.15 (m, 2H) ppm.

Example 2

10 g of triethylamine were added dropwise at room temperature to 11.4 g of glycerol dimethacrylate and 10.6 g of perfluorocyclopentene is 30 ml of acetonitrile. The mixture was stirred at room temperature for 10 hours, and then 100 ml of water were added and the organic phase was separated off. The aqueous phase was subjected twice to extraction with 50 ml of methylene chloride each time. The combined organic phases were subjected to extraction in succession with 50 ml of water, 50 ml of 1N aqueous hydrochloric acid and 50 ml of water. The combined organic phases were subsequently dried over sodium sulphate. Removal of the solvent in vacuo gave 19 g of [3-(2-methyl-acryloyloxy)-2-(2,3,3,4,4,5,5-heptafluorocyclopentenyloxy)]-propyl 2-methyl-acrylate.

Yield: 90% of theory $^{19}$F-NMR data: δ (CDCl$_3$) −115.6, −116.5, −130.1, −159 ppm $^1$H-NMR data: δ (CDCl$_3$) 1.95, (s, 6H), 4.4 (m, 4H), 5.05 (m, 1H), 5.65 (m, 2H), 6.15 (m, 2H) ppm.

Example 3

15 g of triethylamine were added dropwise at room temperature to 15 g of glycerol methacrylate acrylate and 27 g of perfluoro-(2-methyl-pent-2-ene) in 100 ml of acetonitrile. The mixture was stirred at room temperature for 3 hours, and then 300 ml of water were added and the organic phase was separated off. The aqueous phase was subjected twice to extraction with 150 ml of methylene chloride each time. The combined organic phases were subjected to extraction in succession with 100 ml of water, 100 ml of 1N aqueous hydrochloric acid and 100 ml of water. The combined organic phases were subsequently dried over sodium sulphate. Removal of the solvent in vacuo gave 33 g of [3-acryloyloxy-2-(3,3,3-trifluoro-1-(1,1,2,2,2-pentafluoroethyl)-2-trifluoromethyl-propenyloxy)]-propyl 2-methyl-acrylate.

Yield: 96% of theory $^{19}$F-NMR data: δ (CDCl$_3$) −56.3, −59.6, −80.6, −113.4 ppm $^1$H-NMR data: δ (CDCl$_3$) 1.95, (s, 3H), 4.4 (m, 4H), 5.0, 5.4 (m, 1H), 5.65 (m, 1H), 5.95 (m, 1H), 6.15 (m, 2H), 6.45 (m, 1H) ppm.

Example 4

20 g of triethylamine were added dropwise at room temperature to 21 g of glycerol methacrylate acrylate and 21 g of perfluorocyclopentene in 100 ml of acetonitrile. The mixture was stirred at room temperature for 6 hours, and then 100 ml of water were added and the organic phase was separated off. The aqueous phase was subjected twice to extraction with 50 ml of methylene chloride each time. The combined organic phases were subjected to extraction in succession with 50 ml of water, 50 ml of 1N aqueous hydrochloric acid and 50 ml of water. The combined organic phases were subsequently dried over sodium sulphate. Removal of the solvent in vacuo gave 37 g of [3-acryloyloxy-2-(2,3,3,4,4,5,5-heptafluorocyclopentenyloxy)]-propyl 2-methyl-acrylate.

Yield: 93% of theory $^{19}$F-NMR data: δ (CDCl$_3$) −115.4, −116.4, −130.0, −158.9 ppm $^1$H-NMR data: δ (CDCl$_3$) 1.95, (s, 3H), 4.4 (m, 4H), 5.1, 5.48 (m, 1H), 5.65 (m, 1H), 5.95 (m, 1H), 6.15 (m, 2H), 6.45 (m, 1H) ppm.

Example 5

Solutions were prepared from the monomers indicated below by adding in each case 0.5 g of benzyl dimethyl ketal (=photoinitiator) and in each case 79.5 g of butanone (=solvent):

a) 20 g of product from Example 1,
b) 10 g of product from Example 1 and 10 g of BGMA,
c) 10 g of product from Example 1 and 10 g of UMA,
d) 5 g of product from Example 1 and 15 g of BGMA,
e) 20 g of product from Example 2,
f) 10 g of product from Example 2 and 10 g of BGMA,
g) 20 g of product from Example 3 and
h) 20 g of product from Example 3 and 10 g of BGMA.

BGMA=Bisphenol A diglycidyl dimethacrylate.

UMA=Reaction product of one mole of 2,2,4-trimethylhexamethylene diisocyanate and 2 moles of 2-hydroxyethylmethacrylate.

The solutions a) to h) were applied separately using a knife to a polyethylene terephthalate film to give individual wet film thicknesses of 100 μm. These coats were dried at 40° C. for 30 minutes and then exposed in a UV exposure unit (2000 watts) with exclusion of air. The coatings obtained in each case were free from tack, hard, water-repellent and dirt-repellent, and were distinguished by particular ageing stability and resistance to hydrolysis.

What is claimed is:

1. (Meth)acrylates containing fluoroalkenyl groups, of the formula (I)

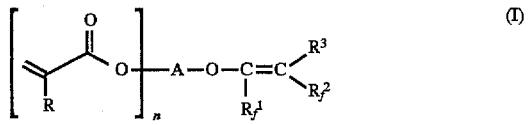

in which

R represents hydrogen or methyl, n represents an integer from 2 to 6,

A represents a (n+1)-valent hydrocarbon radical having 3 to 30 carbon atoms, which optionally contains up to 10 oxygen atoms, up to 6 —OH groups, up to 8 ether bridges, or a combination thereof, $R^1_f$ and $R^2_f$ independently of one another each represent a perfluoroalkyl radical having 1 to 20 carbon atoms, or $R^1_f$ and $R^2_f$ together form a

bridge, in which x represents an integer from 1 to 8, and $R^3$ represents hydrogen, fluorine, chlorine or a perfluoroalkyl radical having 1 to 20 carbon atoms.

2. (Meth)acrylates containing fluoroalkenyl groups, of claim 1, in which in formula (I)

A represents a (n+1)-valent hydrocarbon radical having 3 to 30 carbon atoms and up to 10 oxygen atoms.

3. (Meth)acrylates containing fluoroalkenyl groups, of claim 1, in which in formula (I)

R represents hydrogen or methyl, n represents an integer from 2 to 5,

A represents a (n+1)-valent hydrocarbon radical having 3 to 12 carbon atoms which optionally contains up to 6 OH groups, up to 8 ether bridges, or both and $R^1_f$ and $R^2_f$ independently of one another each represent a perfluoroalkyl radical having 1 to 6 carbon atoms, or $R^1_f$ and $R^2_f$ together form a

bridge, in which x represents an integer from 1 to 5, and, $R^3$ represents fluorine, chlorine or a perfluoroalkyl radical having 1 to 6 carbon atoms.

* * * * *

UNITED STATES PATENT AND TRADEMARK OFFICE
CERTIFICATE OF CORRECTION

PATENT NO. : 5,739,380
DATED : April 14, 1998
INVENTOR(S) : Lui, et al.

It is certified that error appears in the above-indentified patent and that said Letters Patent is hereby corrected as shown below:

Col. 6, line 44    Before " OH " insert -- - --

Signed and Sealed this

Eighth Day of December, 1998

Attest:

BRUCE LEHMAN

*Attesting Officer*     Commissioner of Patents and Trademarks